(12) United States Patent
Lee et al.

(10) Patent No.: US 9,415,229 B2
(45) Date of Patent: *Aug. 16, 2016

(54) DBS AND HEART ELECTRICAL STIMULATION AND MEASUREMENTS WITH MULTIPLE ELECTRODES

(71) Applicants: Chong Il Lee, Stanton, CA (US); Sergio Lara Pereira Monteiro, Los Angeles, CA (US)

(72) Inventors: Chong Il Lee, Stanton, CA (US); Sergio Lara Pereira Monteiro, Los Angeles, CA (US)

( * ) Notice: Subject to any disclaimer, the term of this patent is extended or adjusted under 35 U.S.C. 154(b) by 406 days.

This patent is subject to a terminal disclaimer.

(21) Appl. No.: 13/970,113

(22) Filed: Aug. 19, 2013

(65) Prior Publication Data

US 2014/0107451 A1 Apr. 17, 2014

Related U.S. Application Data

(63) Continuation of application No. 13/053,137, filed on Mar. 21, 2011, now Pat. No. 8,538,516.

(51) Int. Cl.
| | | |
|---|---|---|
| *A61N 1/08* | (2006.01) | |
| *A61N 1/372* | (2006.01) | |
| *A61B 5/04* | (2006.01) | |
| *A61B 5/00* | (2006.01) | |
| *A61N 1/02* | (2006.01) | |
| *A61N 1/36* | (2006.01) | |
| *A61N 1/368* | (2006.01) | |
| *G01R 1/073* | (2006.01) | |
| *A01G 7/04* | (2006.01) | |
| *A61B 5/042* | (2006.01) | |
| *A61B 5/0478* | (2006.01) | |
| *A61N 1/05* | (2006.01) | |
| *G01R 1/067* | (2006.01) | |

(52) U.S. Cl.
CPC .............. *A61N 1/37252* (2013.01); *A01G 7/04* (2013.01); *A61B 5/04* (2013.01); *A61B 5/04001* (2013.01); *A61B 5/6867* (2013.01); *A61N 1/025* (2013.01); *A61N 1/08* (2013.01); *A61N 1/3686* (2013.01); *A61N 1/36185* (2013.01); *A61N 1/372* (2013.01); *G01R 1/07307* (2013.01); *A61B 5/0422* (2013.01); *A61B 5/0478* (2013.01); *A61N 1/05* (2013.01); *A61N 1/0531* (2013.01); *A61N 1/0534* (2013.01); *G01R 1/06744* (2013.01); *G01R 1/06766* (2013.01)

(58) Field of Classification Search
CPC ......... A61N 1/04; A61N 1/05; A61N 1/0526; A61N 1/36128; A61N 1/36146; A61N 1/37252; A61N 1/025; A61B 5/04001; A61B 5/6867
USPC .............. 607/2, 4, 5, 9, 30, 31, 32, 60, 61, 62, 607/66, 68, 70, 116
See application file for complete search history.

(56) References Cited

U.S. PATENT DOCUMENTS 8,538,516 B2 * 9/2013 Lee .................... A61B 5/04001
607/2

\* cited by examiner

*Primary Examiner* — Theodore Stigell
*Assistant Examiner* — Michael Carey (57) ABSTRACT

A picafina device for electrical stimulation and electrical measurements of neural and muscular cells, which is capable of electrical measurements of cells in the neighborhood of the picafina device and also of electrical stimulation at different voltages and current levels.

4 Claims, 9 Drawing Sheets

Fig. 9

DBS AND HEART ELECTRICAL STIMULATION AND MEASUREMENTS WITH MULTIPLE ELECTRODES

CROSS-REFERENCE TO RELATED APPLICATIONS

This application is a continuation of patent application Ser. No. 13/053,137, same inventors as the present one, application date 2011 Mar. 21, which was published on 2012 Aug. 9, under no. US-2012-0203299 A1, which issued on 2013 Sep. 17, U.S. Pat. No. 8,538,516. This application claims the benefit and priority of Provisional Application No. 61/340,920, filing date Mar. 24, 2010 by the present inventors. This application is related to and uses the priority and disclosure of multiple points DBS and heart stimulator and measuring probes of our U.S. patent application Ser. No. 12/586,763, entitled "Method and means for connecting and controlling a large number of contacts for electrical cell stimulation in living organisms", filing date Sep. 28, 2009, published Apr. 1, 2010, under no. US-2010-0082076 A1, now U.S. Pat. No. 8,565,868 issued on 2013 Oct. 22, and application Ser. No. 12/586,562, entitled "Method and means for connecting a large number of electrodes to a measuring device" filing date Sep. 24, 2009, published on 2010 Apr. 1, under no. US 2010-0079156 A1, currently U.S. Pat. No. 8,335,551, issued on 2012 Dec. 18, which are incorporated herein by reference in their entirety, as well as the provisional applications associated with each of these.

BACKGROUND OF THE INVENTION

1. Field of Invention

This invention relates to cellular electrical stimulation in general, for animals and other life forms, as fish and plants, including humans, and neuron, heart muscle, other muscles and organs electrical stimulation in particular, including in particular brain, spine and heart. It also relates to electrical measurements of cells in general, and of neurons in particular.

2. Discussion of Prior Art

It is well established in the field of neurological science that neurons work by propagating electrical signals. This is know to be true whether the neurons are transmitting an order from the brain or other initiating point to another body part, as an order to move the leg forward, which is a complex set of commands, or for a heart beat, that is simpler than a leg movement, delivered to the sinus, or on the other direction, transmitting a sensation from some body part to the central nervous system, as temperature or pain somewhere, or simply thinking, as pondering about the meaning of this very patent disclosure, which is an electrical activity that is completely inside the brain.

It turns out that the brain is divided in parts dedicated to special tasks that are in relative position to each other in the same way in all animals of a particular species and even approximately the same across species. These parts are three dimensional but are called areas by the neurologists. In reality neurologists call area what is really a volume in standard parlance, the place that contains all the neurons involved in apart or in the totality of some particular neurological activity occurs. So, Broca area, as the neurologists call it, is really the Broca volume, as a lay person would, because it is a 3-dimensional arrangement, etc. In the disclosure we most often use the word "volume" because it is a better descriptor, but in established uses, as named regions of the brain, as the Broca area, we use "area". Accordingly, the areas that are used to detect and process vision are located very much the same way in all *H. sapiens*, with little difference to chimpanzees and more differences to cats, which is a consequence of biological speciation and relatedness. The internal parts of an animal are variable in size from individual to individual as much as the external parts are, as size of nose, mouth or hand, but as much as in humans the nose is always above the mouth, each specialized part of the brain has a slightly different absolute size in each individual, but is relatively positioned to each other in the same way in all humans. These brain parts are known by neurologists as areas, as Broca area, Wernicke area, etc. It is also known that constant use can enlarge areas that are requested constantly, as shown by the work with London cab drivers.

The brain of *Homo sapiens* is now all mapped, that is, the function of all areas is known to the neurologists. Accordingly, the Broca area is responsible for speech and its position is known, the Wernicke area is responsible for hearing, also at a known location, and so forth, and their position in the brain is well known to the neurologists. Yet, though their relative position is the same, their absolute position with respect to some external mark is not the same in all humans, among other reasons because humans come in different sizes, but also because even two humans of the same height have noses, hands, hearts, livers and Broca and Wernicke areas of not exactly the same size, and even the same exact shape. Eric R. Kandel (Kandel (2000)) gives a good overview of the current state of the art from the academic point-of-view.

Accordingly, two fields have been developing: neurological research and correction of neurological disorders. These have advanced to the point that it is now common, ordinary, daily practice, to measure electrical signals in neurons, and also to add electrical stimulation to them to change their actions. The former, neuron measurements, are only rarely done in humans, and done in experimental animals under close monitored conditions, after receiving approval of some internal reviewing board that oversees animal research. Naturally that in mammals, experiments are under closer control than in fish, and more loosely control on insects and the like, because few humans care much about the *Drosophila melanogaster*, a feeling that is reciprocated, the inventors believe.

The latter, electrical stimulation, is a common surgery practiced today, mostly to control Parkinson's disease, but in smaller numbers for other neurological malfunctions too, as epilepsy, and other disorders. Electrical stimulation is also done for pain control and for organ stimulation (including increasing and decreasing organ activity), as for appetite control, bladder control and the like.

Given that many of the readers here may be from the biological sciences or medical fields, we define a common term used in electronics. In the context of this text here, "electrode" is the ending portion of the stimulating device, from which electrical current is injected into the cells, as neurons, muscle, etc. Also known as pad. Associated with it is the term "measuring tip", "measuring pad", "stimulating tip" and "stimulating pad", These are the very tip of the measuring/stimulating wire, sometimes referred as electrode in current art, made of metal or some other electrically conducting material. In current art devices the measuring tip is generally at the end of a thin, stiff wire, typically 100 micrometers diameter, separated by 100 micrometers, or more, while in our invention the measuring tip is a metallic area as small as a few micrometers, typically 5 micrometers but can be less or more according to the need, separated by as little as 5 micrometers, at the surface of the device of our invention. Current art is capable of manufacturing measuring tips for our invention that are less than one micrometer in diameter, and the shape is not necessarily circular. Another term in use in this field, this one self-explanatory but which we explicitly define, is "neural sensor". As used here, the term "neural sensor" means an implantable device for sensing neural signals. Examples of neural sensors include microwire electrode arrays, optical sensors, microwires, magnetic field detectors, chemical sensors, and other suitable neural sensors which are known to those of skill in the art upon consideration of the present disclosure. Accordingly, electrodes for both neuron measurements and stimulation have been developed and are commercially manufactured by a number of companies. Electrical neuron measurements are not widely known to be done in the lab, though they are, but electrical stimulation is widely known in its incarnation as heart pacemakers, that are designed to stimulate the heart muscle by adding an electrical pulse to the one delivered at the sinus node. A pacemaker is used when the electrical pulses to the sinus node becomes defective.

Therefore for both neuron measurements and for neuron stimulation, there exists a need to reach a number of neurons, the position of which is difficult to determine with respect to some external feature, as the top of the head or the mammary gland, from which to go to the hypothalamus in the brain from a 1 cm. hole on top of the head, or the sinus node in the heart, from a vein in the clavicle. This is so because, though the relative position of the neurons and cells responsible for each task is generally the same in animals of the same species, the absolute distances is not the same from animal to animal. It follows that it is very difficult for a neurologist to know exactly where the inserted electrode is, whether he/she is interested in making an electric measurement in the brain of a laboratory animal, or in implanting an electrode on a *Homo sapiens* to control Parkinson's disease. To counter this difficulty, electrode arrays have been introduced both for measurements and stimulation. For measurements there exists arrays composed of several dozen electrodes separated by 50, 100, 250 micrometers, and for neuron excitation, generally larger distances, but details depend on the particular situation. Neither of these have been able to make use of a very large number of electrodes because of the difficulty in passing a large number of wires to connect them to the outside world. Our inventions U.S. patent applications Ser. No. 12/586,763, filing date Sep. 28, 2009, published 2010 Apr. 1, under no. US-2010-0082076 A1 now U.S. Pat. No. 8,565,868 issued on 2013 Oct. 22, and application Ser. No. 12/586,562, filing date Sep. 24, 2009 published on 2010 Apr. 1, under no US 2010-0079156 A1, currently U.S. Pat. No. 8,335,551, issued on 2012 Dec. 18, which are incorporated herein by reference in its entirety, as well as the PPA associated with each of these, disclosed methods and means to connect a much larger number of electrodes, in one case to measure, on the other case to stimulate. With the addressing method disclosed in these patents, instead of having n wires to activate each electrode separately, the same n wires used as an address bus can generate 2 power n (2-super-n) addresses, which in turn can select that many electrodes. For example, one commonly used brain stimulator marketed by Meditronic uses 4 connecting wires to stimulate any one of a set of 4 electrodes at the end of the lead. Using the same 4 wires as an address bus, there is the possibility of selecting 2-super-4=16 separate electrodes, which allows for a much larger selection of points to start electrical stimulation. Yet if these inventions substantially decreased the number of wires to make the necessary connections to a large number of electrodes, it is possible to decrease the number of wires even further, which is very important in an implanted device which must be as little intrusive as possible to make.

BACKGROUND OF THE INVENTION—OBJECTS AND ADVANTAGES

Former devices for electrical stimulation, whether used for brain (as DBS), heart (as in pacemakers), chronic pain control, muscle, organs and others, used a very limited number of electrodes as initiation points of the electrical stimulation. Similar observation applies to electrodes used to measure electrical cell activity. This was a consequence of the limited space available to pass wires between the battery and control electronics and the actual stimulating devices (of measuring devices). Our inventions disclosed in U.S. patent application Ser. No. 12/586,763, filing date Sep. 28, 2009, published 2010 Apr. 1 under no. US-2010-0082076 A1 now U.S. Pat. No. 8,565,868 issued on 2013 Dec. 22 and U.S. application Ser. No. 12/586,562, filing date Sep. 24, 2009, published on 2010 Apr. 1, under no. US 2010-0079156 A1, currently U.S. Pat. No. 8,335,551, issued on 2010 Dec. 18, disclose methods to increase the number of available stimulating electrodes for both electrical stimulation and for electrical activity measurements as well, while still keeping the number of wires relatively small. These patents disclose the use of an addressing system to select one electrode or a set of electrodes to be the origin of electrical stimulation, or to be the origin of electrical measurements, from a large number of available electrodes, while the addressing wires are in smaller number than the electrodes themselves. Indeed, with n wires it is possible to generate 2-super-n addresses. For example, with 4 wires it is possible to create 2-super-4=16 different addresses that uniquely identify 16 different electrodes. The addressing system disclosed in our patents become more impressive as the number of bits in the address bus increases. Indeed, with 10 bits (that is, with 10 addressing wires), it is possible to generate 2-super-10=1024 different addresses, identifying 1,024 different electrodes. In other words, with 10 bit-wide address bus, not much many more wires than existing stimulators have, it is possible to have 1024 separately controllable electrodes, a number that, given the small size of the devices is virtually infinite.

Yet the addressing system still suffered from the use of too many wires to create the necessary addresses for each individual or group of electrodes or pads, because of the extremely small available space available in devices implanted inside the body of animals. This invention discloses an improvement on the earlier method of addressing with a bus composed of a plurality of wires, using instead a serial method to exchange digital information from the microcontroller housed in 110 and the electrical stimulating electrodes 140, thus reducing the number of wires to two (counting the return wire), or even one, if the power return is also used for serial return, or if the body of the animal is used as ground or return. Accordingly, with the system described in this patent disclosure, three wires (address/data digital transfer, electrical power and ground) or even two, if the body of the animal is used as ground or return wire, suffices for a working electrical stimulator with as many electrodes as one wishes to have—an unbounded number of electrodes. Extra wires are also possible, for example, to allow the possibility of measurements simultaneous with stimulation, or for stimulation at different voltage (or current) levels.

Accordingly, several objects or advantages of our invention are obviating the difficulties of running multiple wires in the supporting structure to reach the electrode points at the distal end of the inserting/supporting structure for both cell measurement and stimulation (neurons, as in brain, spinal cord and elsewhere, muscles, as in heart and others, organs, as in stomach, bladder and others).

Another object and advantage or our invention is to cut down on the number of address wires that run through the supporting structures to the cell stimulator or to the cell measurement pads, which are needed to select which electrodes are to be used in the particular case.

Another object and advantage of our invention is to decrease the manufacturing difficulties and consequently manufacture costs of addressable electrodes for neuronal measurement and stimulation.

Another object and advantage of our invention is to decrease the number of wires used to address the electrodes used for either measure or to stimulate, therefore decreasing the possibility of malfunction and the cost of the device as well.

Further objects and advantages of our invention will become apparent from a consideration of the drawings and ensuing description.

SUMMARY

Our invention is a simplification of the addressing method to select which electrode tips are chosen to read electrical neuronal activity or to deliver a stimulating current to the neurons. It describes a single serial line, instead of a plurality of parallel addressing lines, which substantially decreases the number of wires necessary for the operation or stimulating and measuring electrodes implanted in living organisms, wires that have to be passed through a very small space which may not have enough space for many of them. We also disclose the possibility of a small number of wires to function as a parallel-serial mixture, in which data is transferred serially over more than one wire at a time, which decreases the depth of serialization by the same factor as the number of wires that carries the data.

DETAILED DESCRIPTION

Figure 1:
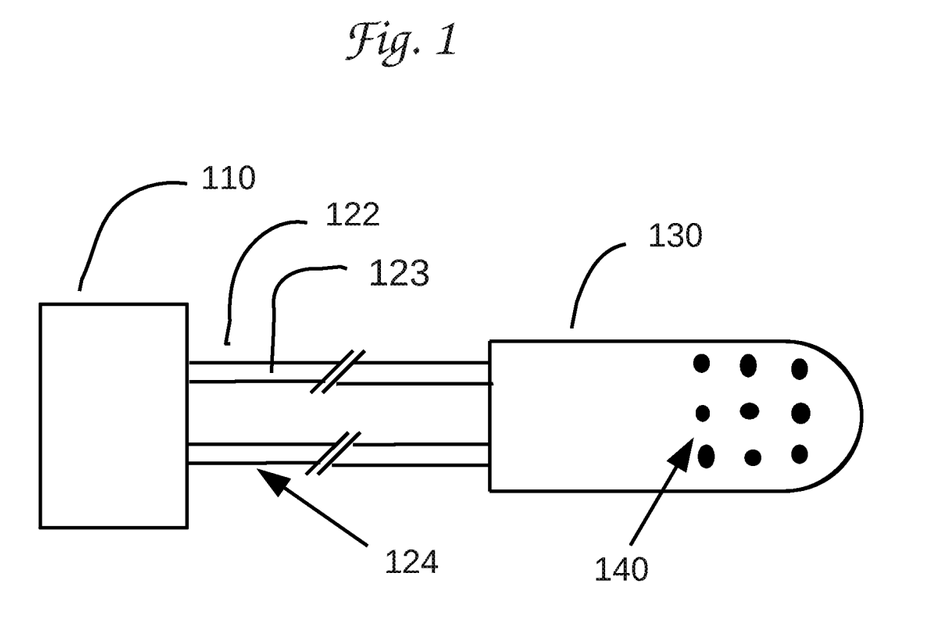
FIG. 1 depicts a complete schematic view of the main embodiment of our invention while omitting the details.

FIG. 1 depicts a complete schematic view of the main embodiment of our invention, while omitting the details. The body of our invention is shown as number 130 in FIG. 1. We call it "picafina". Picafina is a supporting structure used by the math embodiment of our invention, generally similar to the devices used in Deep Brain Stimulation but potentially with far more tips or electrodes than DBS devices of current art, which is strong enough to allow it to be inserted in the brain or other body structures, and which contains the necessary wires for connecting the measuring tips and the address decoders with the controlling and measuring instruments. For use in human animals, he dimension of a type I picafina is approximately the diameter of a drinking straw (1.5 mm.), its length being the necessary to reach the desired depth in the body. For smaller animals (as a mouse), the picafinas would be accordingly smaller, both in diameter and length, while for larger animals (as a whale or an elephant), the picafinas would be accordingly larger. The reader is encouraged to study it carefully, as it embodies the basic principle of our invention. The main embodiment assumes a brain stimulation, of the type generally known in neurology as DBS (Deep Brain Stimulation), but other applications are possible, as described in the sequel, particularly for other brain and neuronal stimulation (pain, epilepsy, and others), and for heart stimulation, or pacemaker, or for organ stimulation, as stomach, bladder and the like, or for artificial limb motion, or to induce motion on limbs that lost neural activation, all with the necessary adaptations for each particular application. In FIG. 1 one sees a box 110, usually housed in the patient's chest, which contains the battery and the control electronics, in this case the electronics also contains an address generator, as described in our patent pending Ser. Nos. 12/586,562 and 12/586,763, application dates Sep. 24, 2009 and Sep. 28, 2009, entitled "Method and Means for Connecting a Large Number of Electrodes to a Measuring Device" and "Method and Means for Connecting and Controlling a Large Number of Contacts for Electrical Cell Stimulation in Living Organisms" respectively, and in addition, as disclosed in this patent, also a parallel-to-serial converter (new invention, not part of the above cited patent applications), which is capable to serialize the (usually binary) address required to select a particular electrode on the surface of the picafina and then send the information in serial form in just two wires 122 and 123, as shown. From the battery/electronics box also leaves the power wire and its return 124, that is, the wires that carry the stimulating pulses. Some versions may use more than one power wire to accommodate several levels of voltage (current) at the electrodes, or simultaneous measurements at different sites. In this embodiment a total of just five wires are used from the battery/electronics box until the brain stimulator on the head. In the brain implant there exists, in the main embodiment of our invention one serial-to-parallel decoder for each set of radially distributed electrode set, that is, electrodes at a fixed z-distance from either end of the picafina, around its perimeter. These serial-to-parallel converters may serve more then one z-distance (more than one circle on the brain picafina), or else less than one.

Figure 2:
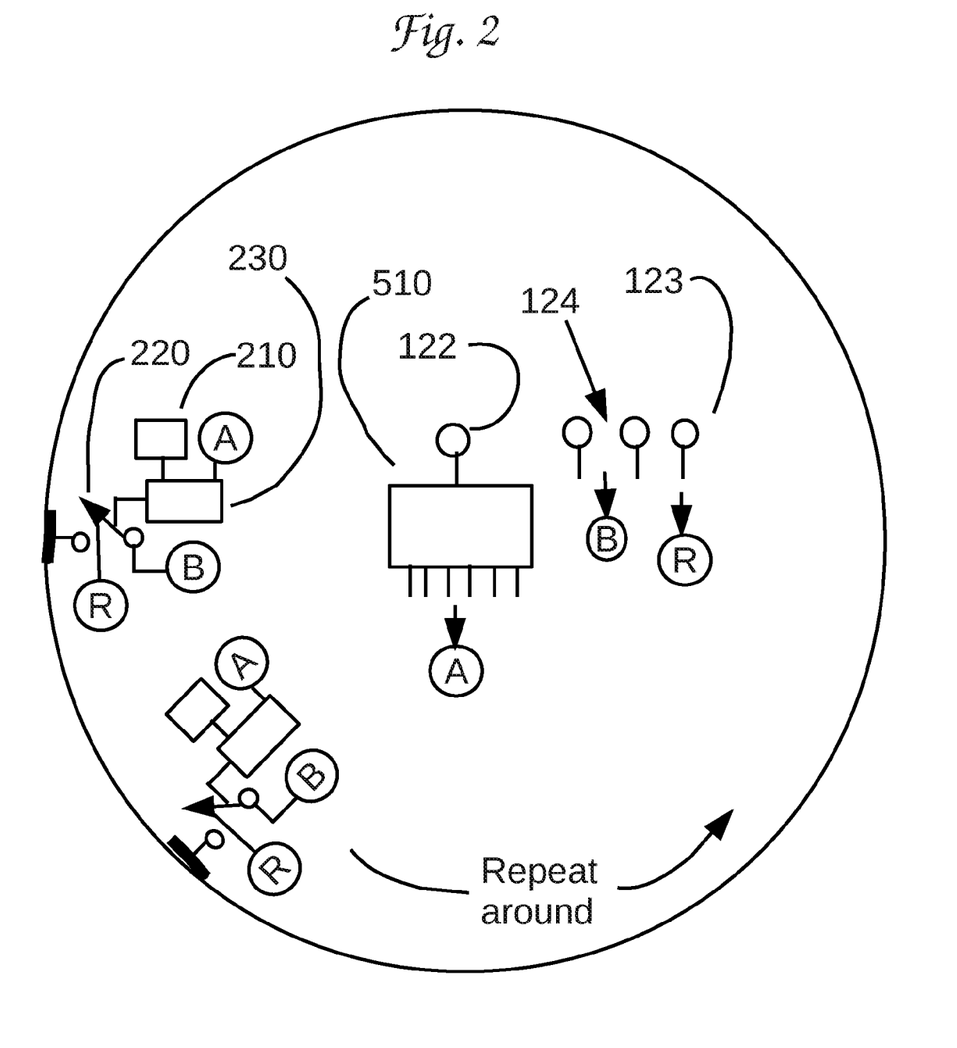
FIG. 2. This figure displays a cross section of the main embodiment of the DBS-type picafina of our invention, a cross section perpendicular to the picafina's main longer, vertical axis.
Figure 3:
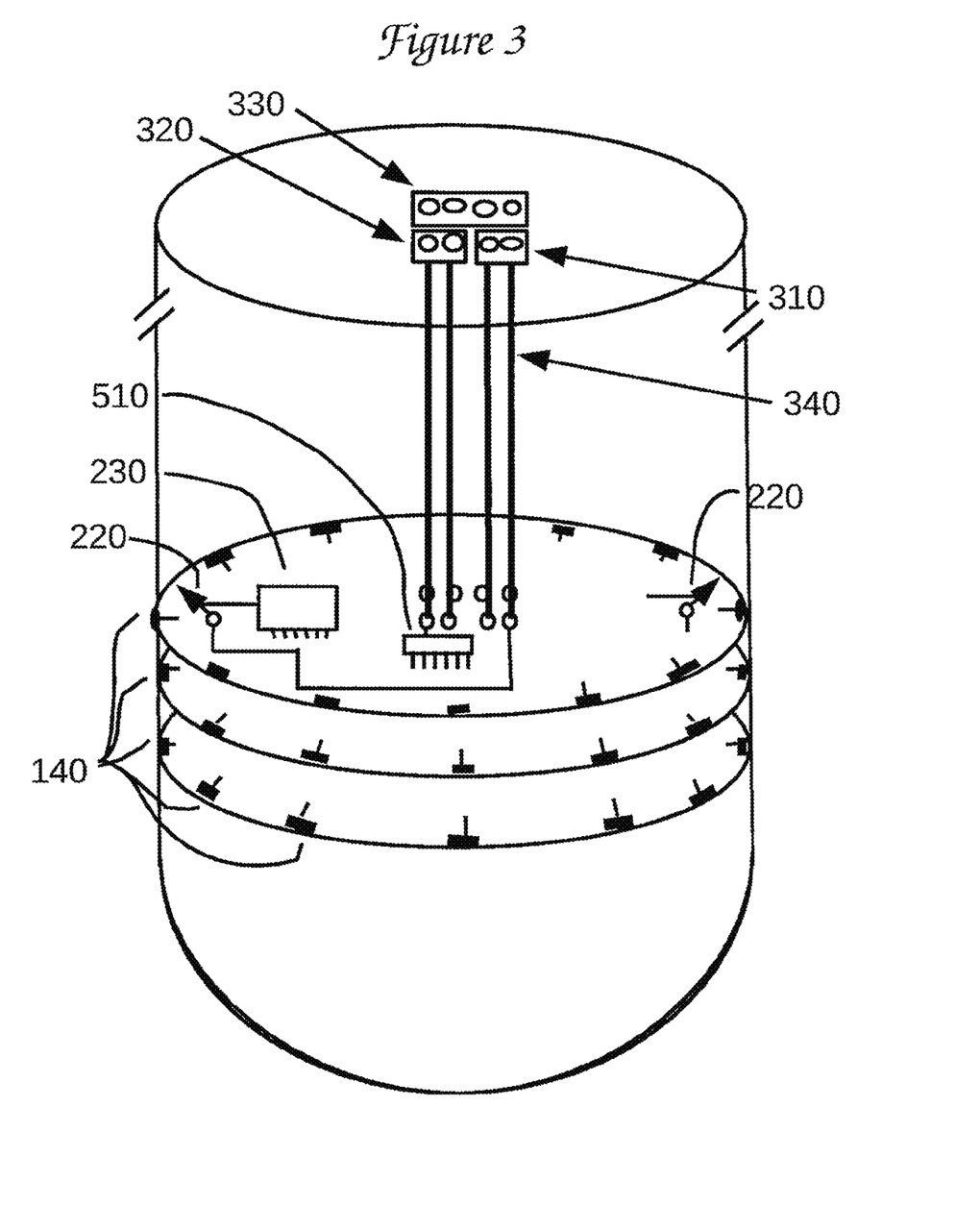
FIG. 3 A perspective view of a DBS picafina, one of the possible embodiments of our invention.
Figure 4:
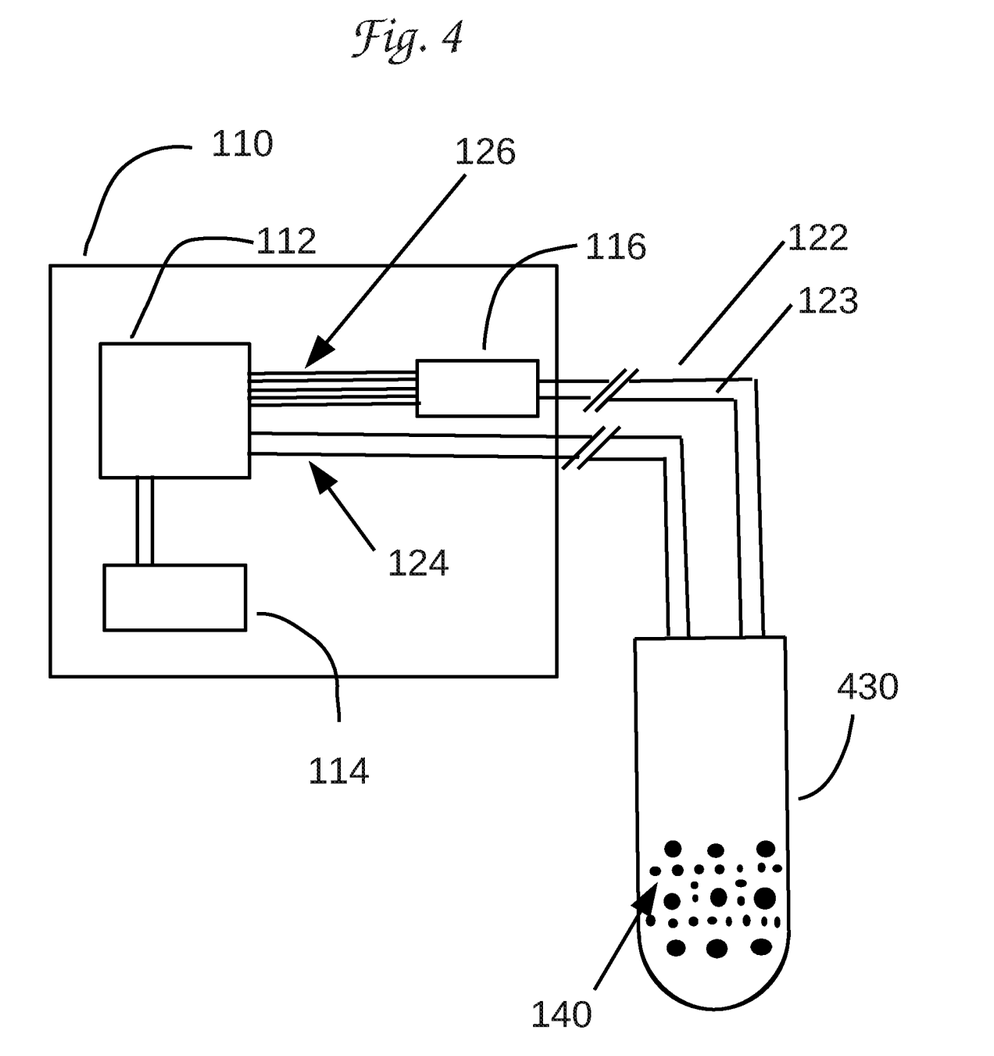
FIG. 4. Serial address generation.
Figure 5:
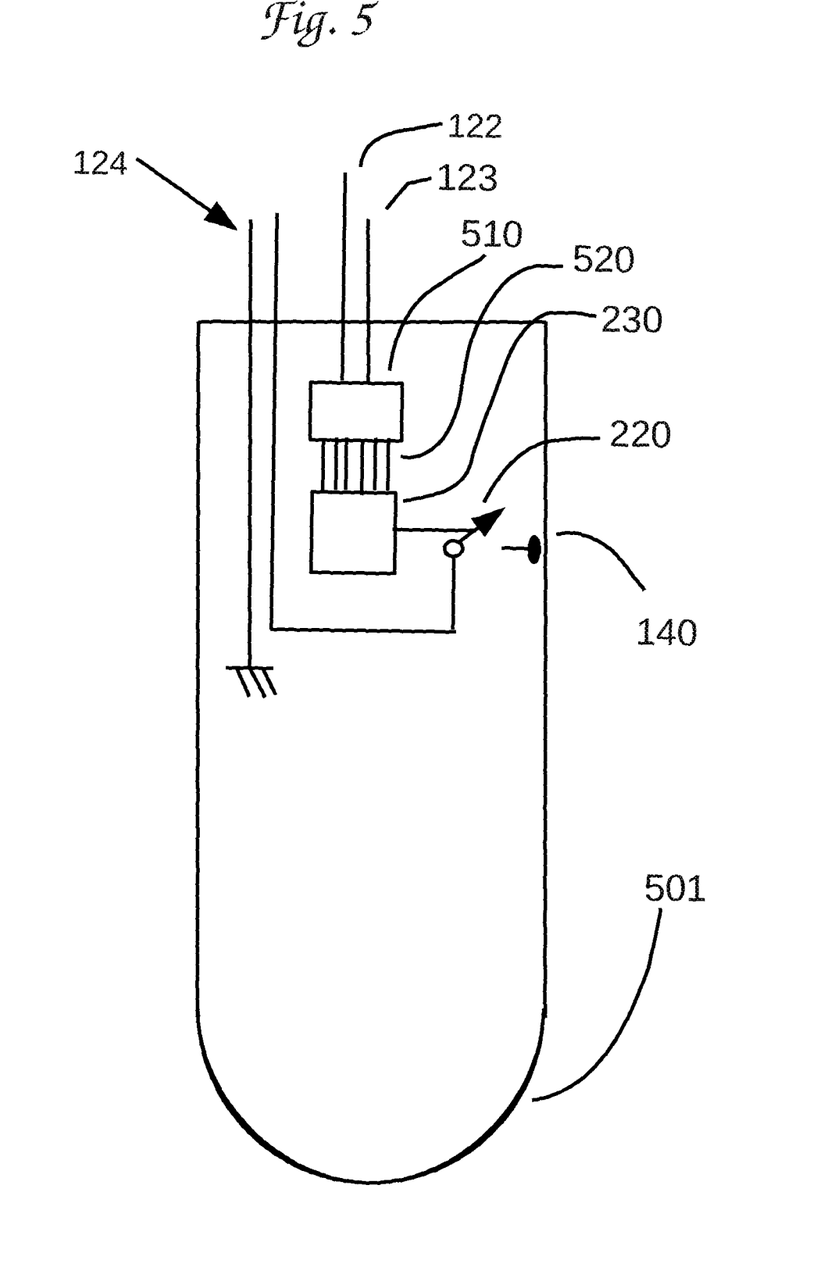
FIG. 5 displays the case for a dedicated serial-to-parallel converter for each electrode tip, or pad.

In this FIG. 1 one sees a box indicated as BAT1, usually housed in the patient's chest, which contains the battery and the electronics. In this case the electronics, besides the current art electronics, also contains an address generator, as described in our U.S. patent application Ser. No. 12/586,763, filing date Sep. 28, 2009, published number US 2010-0082076 A1, on 2010 Apr. 1, now U.S. Pat. No. 8,565,868 issued on 2013 Oct. 22 and U.S. patent application Ser. No. 12/586,562, filed date Sep. 24, 2009, published number US 2010-0079156 A1 on 2010 Apr. 1, now U.S. Pat. No. 8,335, 551 issued 2012 Dec. 18, and also a parallel-to-serial converter, which is not disclosed in these two patent applications, which is disclosed in this patent application, which is capable to serialize the binary address required to select a particular electrode on the surface of the DBS picafina, and then send the information in serial form in just two wires, as shown. The serial form of address, data and control cause From the battery/electronics box 110 also leaves the power wire and its return (sometimes referred as ground), that is, the wires that carry the stimulating pulses. In this embodiment a minimum of just four wires are used from the battery/electronics box until the brain stimulator on the head, with the possibility of more wires for control, but not used in the minimal embodiment of our invention. In this main embodiment control signals are also sent via the same serial connection as the addresses. In a variation with separate control wires, the total number of non-power wires would be three or more, instead of 2. It is also possible to use a common return (ground) wire for both digital and analog lines, further reducing the number of wires to three (power, serial addressing+ control and return common to both), and it is also possible to use the body as a common ground, or return, further reducing the number of wires to two (power and serial addressing+ control). In the brain implant there exists, in the main embodiment of our invention, one serial-to-parallel decoder for each set of electrodes at the same distance from the picafina endings, as shown in FIGS. 2 and 3. FIGS. 4 and 5 elaborate on this main embodiment, showing details of the box containing the battery/electronics and of the picafina, or device implanted in the brain.

FIG. 2 displays a cross section of the main embodiment of the DBS-type picafina of our invention, a cross section perpendicular to the picafina's main longer, vertical axis. The circle is on the outside surface of the picafina, at a fixed distance to each end of it. On its outside surface there are a number of pads, or points from which the electrical stimulation originates. Each of these pads may or may not be energized, depending on whether the switch SW is closed or open. Switches SW are closed or open depending on the address written on A is equal or not equal to the local address LA of the particular address decoder ADec. Writing different addresses, different switches are closed, energizing the corresponding pads. Switch SW may have a time delay, which keep it closed for a predetermined time after address matching at ADec. Alternatively, switch SW may become permanently closed after an address match on ADec, until a different pulse comes, from a different circuit (not shown), which deselects it (SEL/SEL-bar are common digital electronics jargon, the bar being the standard logical indication of negation, so SEL/SEL-bar means Select/not select). Within the plane of the displayed cross-section, the wires running along the picafina, which are perpendicular to the cross-section shown, connect to the parts as shown, then are printed circuits made by any of the existing technologies, as PC boards, or as die manufacturing, or a combination of these. These wires can occupy more than one layer, including vias for crossing, connecting the incoming the two serial wires to the serial-to-parallel converter, connecting the decoded parallel wires to each ADec and the power wires to each of the switches. SEL-bar, or deselect wires are not shown.

FIG. 3 is perspective view of a DBS picafina, one of the possible embodiments of our invention, showing the top or the picafina with the entrance points for the wires, and one of the layers of pads, at a fixed distance from the picafina's ends. This figure is similar to FIG. 2, adding to FIG. 2 the visual positioning of the layer of pads within the whole device. FIG. 3 shows less details of the circuitry in the layer while showing where it is within the whole device.

FIG. 4 shows a serial address generation. The microcontroller (or one of its equivalents) generates the addresses of the stimulating points to be used, then these binary addresses are conveyed from the battery/electronics box in serial format (two wires or one wire only,) to the picafina, where the serial is converted back in parallel binary for use.

FIG. 5 displays another alternative view of the brain-type stimulator, or picafina. Inside the picafina there are a multiplicity of serial-to-parallel converters that create the binary addresses to select the electrical contacts to be used. FIG. 5 displays the case for a dedicated serial-to-parallel converter for each electrode tip, or pad. A more typical application would have one serial-to-parallel converter at each planar group of electrodes at a fixed distance from the picafina's extremity (or in a circular arrangement on the picafina).

Figure 6:
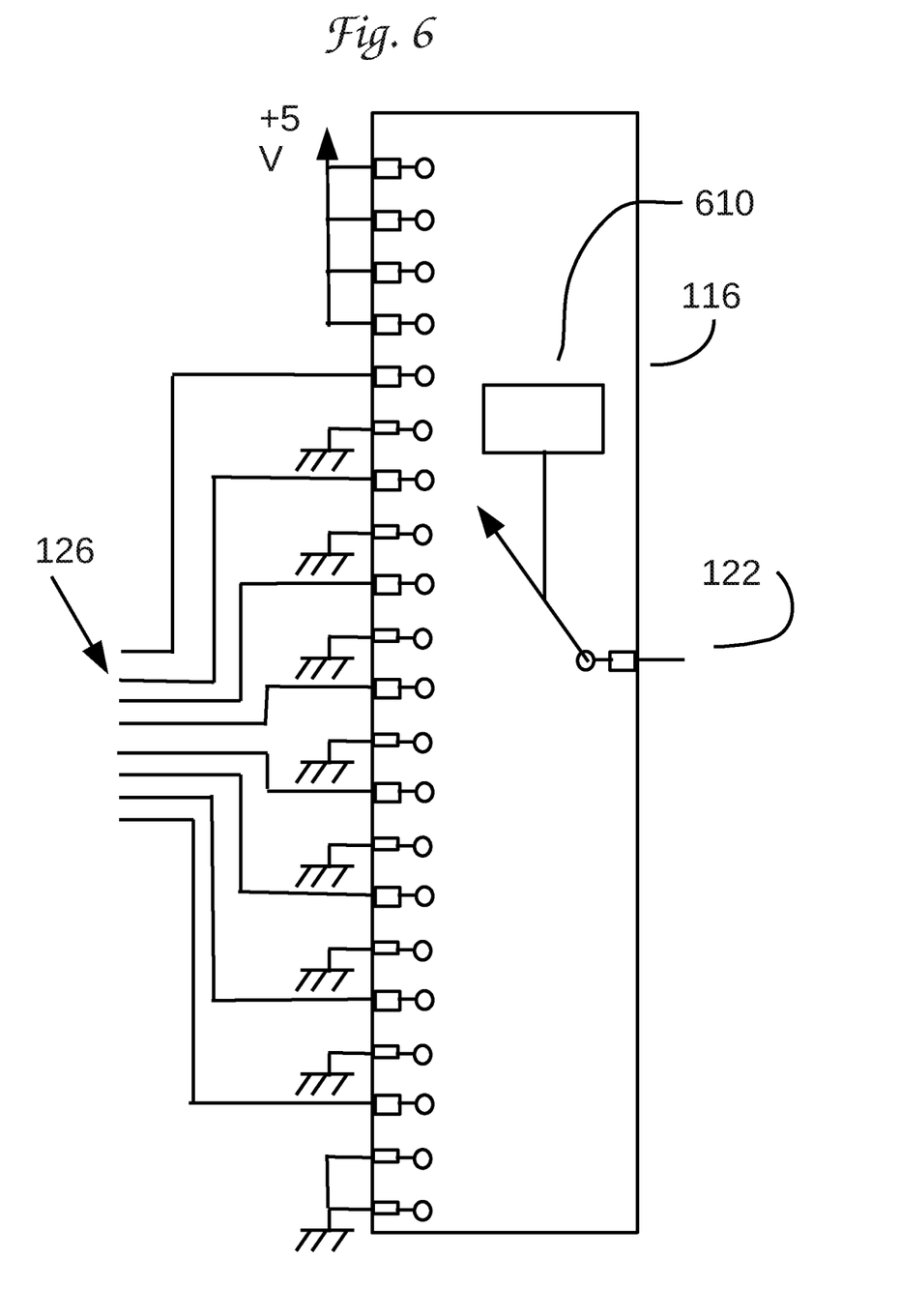
FIG. 6 A possible implementation of a parallel-to-serial conversion. This is shown as an exemplary case only. Note that following electronics practice there is an implied ground which is not shown in this drawing for simplicity.

In the main embodiment the serialization of the pad address is made with a circuit as shown in FIG. 6 or any of its equivalents. This is shown as an exemplary case only, omitting the details of the necessary logic and the transistor connection necessary to implement the indicated circuit. It is not necessary to show the details because these are part of the standard art of digital electronics, the art of constructing semiconductor switches, and the art of digital logic, which are not part of this invention and are known to the persons familiar with the appropriate branches of the art of electronics. Moreover, this particular exemplary method of data serialization is not necessary altogether, because there are many existing off-the-shelf technologies to implement this function, as described in the sequel. When using one of the existing off-the-shelf technologies, it is expected that the actual die will be used, integrated within the structure of the electronics. The use of the die, as opposed to the packaged chip, is particularly important in the stimulation extremity of the device (the picafina, or DBS electrode wand), because the picafina is necessarily of small diameter, offering little space, current art being 1.3 mm diameter. The particular implementation shown in FIG. 6 is shown only as an example of the main idea, omitting the details, not intended for real use, parallel-to-serial converters being a mature art in electronics and not part of this invention.

In the sequel we will be using a term in common use in electronics, where "to latch" means the capability to keep some particular configuration, or output, or logic, or selection, even after the selecting source, etc., is no longer active, or even if the selecting source is changed to a different value. Another way to look at it is that a latched device has memory to keep a configuration when instructed to do so. A standard light switch is an example of a latch because it keeps the last state it was set by a human being, either on or off, until it is again changed to a new state by another human. In this main embodiment, it is envisaged that the cycle could start with a RESET signal, turning off all switches (no power in all electrodes or pads), which would be followed by a sequence of addresses sent on the serial line, which are decoded at the picafina end, which in turn would turn on the appropriate switches, connecting the corresponding pads to the power wire through a latch which in turn would keep the pad on until a RESET signal is sent. A plurality of pads can be on at the same time, as disclosed on our two regular patent applications referred above.

The main embodiment uses an USB type of serial hardware, but adapted to the use of the two digital lines only, the analog (or power) lines of it being separate from the USB serial connection.

Figure 7:
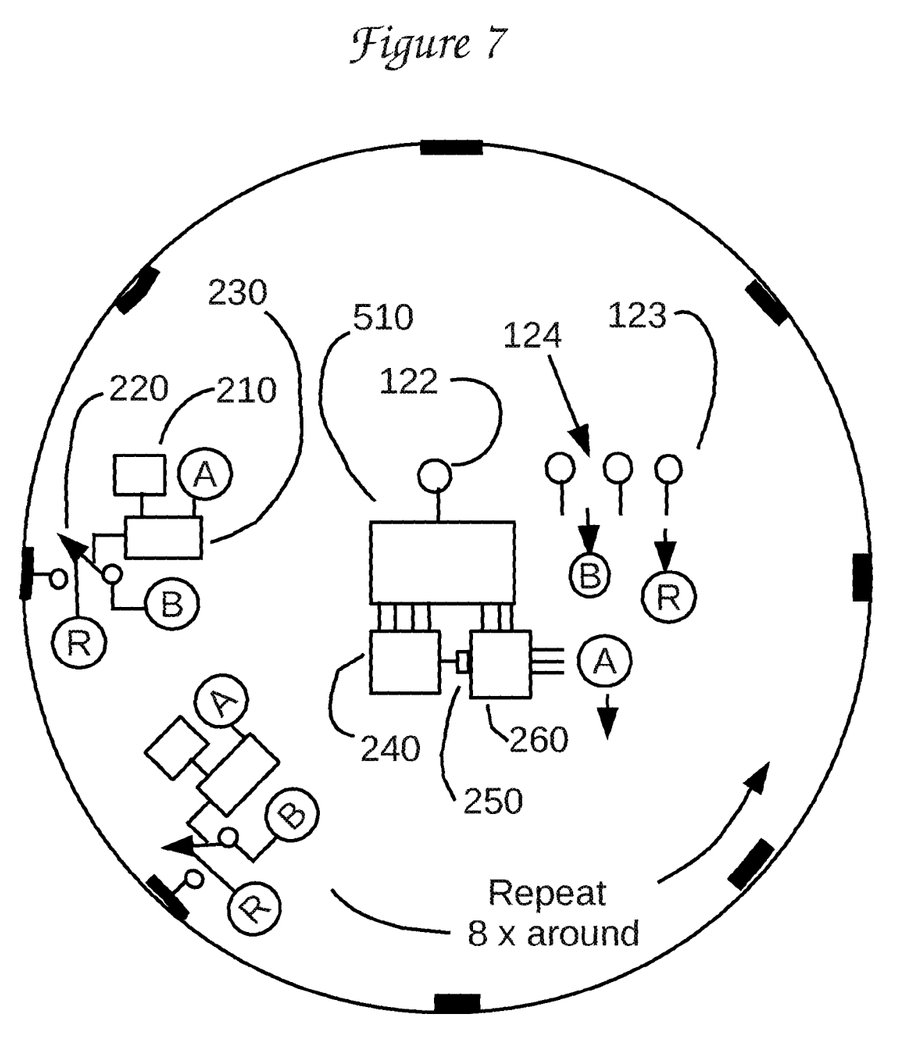
FIG. 7 An alternative implementation of the addressing system, in which the serial-to-parallel converter is also associated with an address decoder to select or not select a particular group of pads.

The main embodiment is constructed from a multiplicity of layered planar circuits at varying distances from one of the DBS extremities as shown in FIGS. 2, 3 and 7. Each of these circuits is constructed with printed circuit (PC) technology, as developed for the printed circuits that form the backbone of computer technology, as motherboards and expansion cards as video cards, extra USB cards, and the like. Such cards generally are made with several layers. FIG. 7 is an alternative implementation of the addressing system, in which the serial-to-parallel converter is also associated with an address decoder to select or not select a particular group of pads, in the situation depicted, 5 lines are used to select each of the 32 (2 power 5=32) group of planar pads, and 3 lines are used to select one of the 8 pads (2 power 3=8) on the periphery of the group. Such an arrangement has the advantage of decreasing the number of wires running inside each planar group. The planar geometry is particular to a possible arrangement, it being possible to have other geometries too.

Some Examples of Intended Use

One example of intended use is an electrode for DBS (deep brain stimulator), of the type currently manufactured by Medtronic (Medtronic (n/d)) or by St. Jude Medical (StJude (n/d)).

Another example of intended use is any of the brains stimulators used for epilepsy control.

Another example of intended use is a cortical brain stimulator, of the type used for stroke rehabilitation (Ref Harvey_2007).

Another example of intended use is the heart pacemaker, of which there are many models and many manufacturers, for example Medtronic (Medtronic (n/d)), by St. Jude Medical (StJude (n/d)).

Another example of intended use is a stomach stimulator used for appetite control.

Another example of intended use is a bladder stimulator used for bladder control.

Another example of intended use is a chronic pain control stimulator device.

Another example of intended use is for research, in which one or a plurality of small electrodes can be selected by telemetry to measure electrical activity at various points near the surface of the device. When measuring more than one electrode using a single transmitting wire, the addressing system would rotate among the several desired electrodes. A typical electronic measurement, including analog-to-digital conversion is of the order of microseconds, much faster than the typical neuronal activity that occurs in a time of milliseconds.

Another example of intended use is a mixed-use device, which uses some electrodes for electrical stimulation and other electrodes for neuronal activity measurements. This mixed use has possibilities in both clinical and research environments as well. In clinical situations, measurements of the prevailing neuronal activity can be interpreted by the microcontroller MC1 then used to determine, according to some programming, which of several possible electrical stimulations is the best for the existing situation. In research situations, instead of just measuring neuronal activity at some site, at most correlating it with external inputs, as light/dark, sound/no-sound, cold/hot, different types of emotions, etc, the researcher can induce electrical stimulation in some neurons then observe the consequence in other neurons.

Another example of intended use is a three-type mixed-use device, which uses some electrodes for electrical stimulation, other electrodes for neuronal or other cell activity measurements, and still other electrodes that are electrically isolated, which functions only as field shaping surfaces.

Operation of Invention

Figure 8:
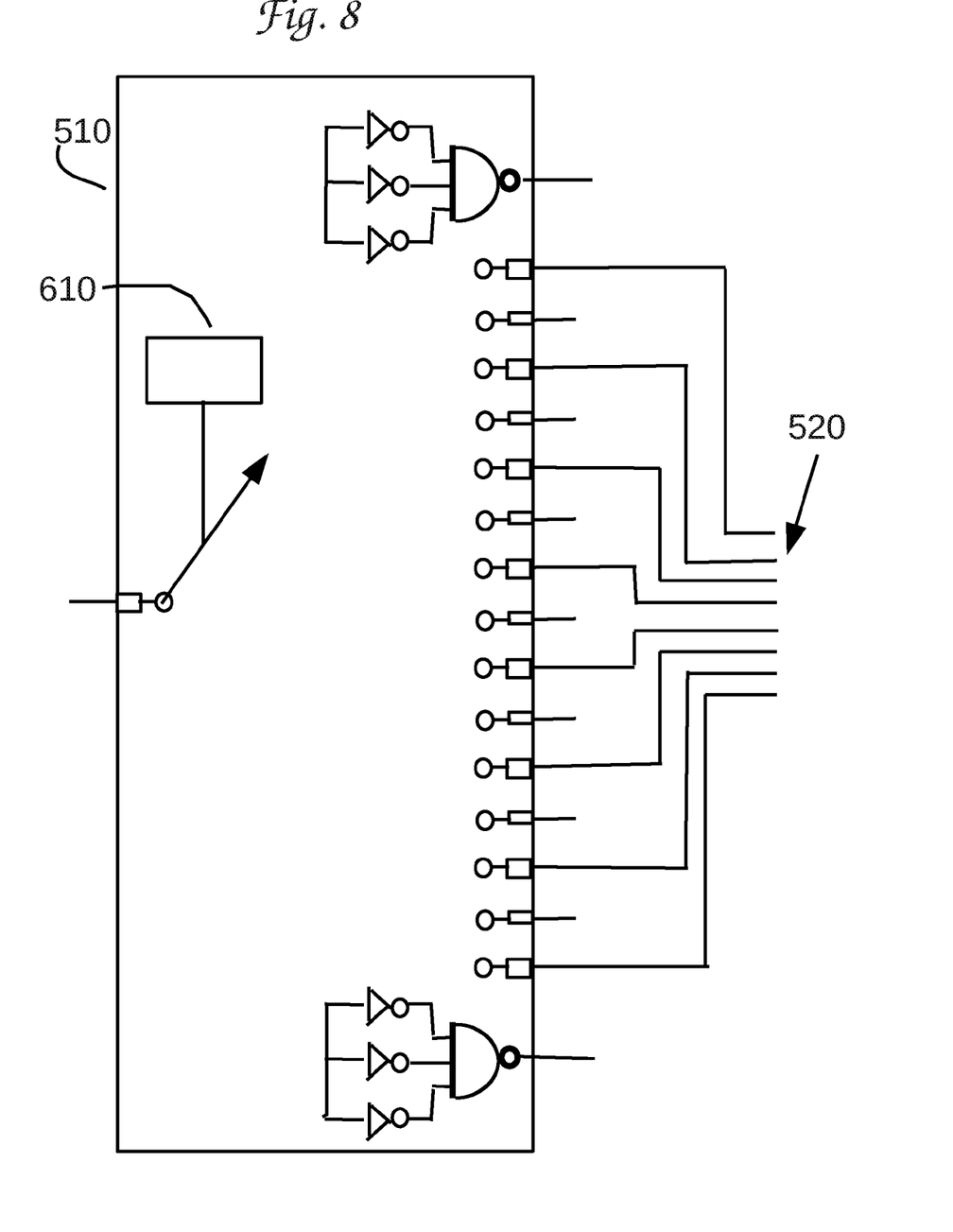
FIG. 8 A possible implementation of a serial-to-parallel conversion. This is shown as an exemplary case only.

The operation of our invention is the conversion, preferably still in the chest's battery/electronics box, of binary, parallel addressing lines to serial form, then the transport of this information from the battery pack/electronics to the picafina in serial form, than its reconversion to parallel form near the point-of-use inside the picafina. This is accomplished with a parallel-to-serial converter at the battery pack/electronics box (110), shown on FIGS. 4. The data, which usually is the addresses of the electrodes that will be injecting current in the patient's brain, therefore selecting the positions in the brain to receive electrical stimulation, which in turn select the neurons that will be electrically stimulated, is then sent in a smaller number of wires to pass over the limited space available. The operation is completed inside the brain picafina, preferably, but not necessarily only, at each planar layer that serves a group of electrodes at the same distance from the picafina's extremities, as shown in FIGS. 5, 2, 3 and 8. FIG. 5 displays a general arrangement for the brain-type picafina, while FIGS. 2 and 3 display the general lay-out on one of the several planar connectors that receive the electrical connections from 110 then distributes them to the appropriate electrodes at the surface of the picafina. The surface of the picafina is the external surface seen in FIGS. 5 and 3, which are in perspective, and is the perimeter of the circle shown in FIG. 2, which is a cross-section of it perpendicular to its main axis along which the main wires run through it. FIG. 8 is a possible implementation of a serial-to-parallel conversion. This is shown as an exemplary case only. Many others exist in textbooks, manuals, etc., this being a mature field in electronics, which is not part of our invention. Note that following electronics practice, there is an implied ground which is not shown in this drawing for simplicity. Also not shown is the logic which starts the connection of the bits to the appropriate output pins (BIT0, BIT1, . . . BIT7 in this case), and other necessary logic for the external circuit to grab the assembled parallel sequence. These are details not part of this invention, it being part of a mature field in digital electronics and data transfer. As it will be appreciated by the persons familiar with the art of digital electronics and digital logic, the output of the AND gate at the top provides the initiation signal for the beginning of the initiation of the process, and the output of the AND gate at the bottom provides the end signal. This particular implementation, as drawn, only works for 8-bits, which is only an exemplary implementation, it being possible to do the same with more and with less bits, as it will be appreciated by the ones familiar with the art.

The main embodiment uses a software code which sends bits of 1 microsecond width (whether high or low) and indicates the initiation of a data transfer with an attention sign composed of a sequence of 10 shorter bits alternating high and low, of pulse-width 0.25 microseconds each, which clearly differentiates the attention sign from the data bits. After each address is sent from the microcontroller MC1 in 110 to the stimulator device ST1, this latter sends back a confirmation of data/address received, including its value, for confirmation. Upon confirming that the data/address value the microcontroller MC1 continues with the next byte, or else re-sends the previous byte. This particular method of data/address transfer should not be taken as a limitation on the invention, many other type existing, this being a mature topic in the field of data transfer in digital electronics, any other being acceptable and this particular one being used as an exemplary case only.

Figure 9:
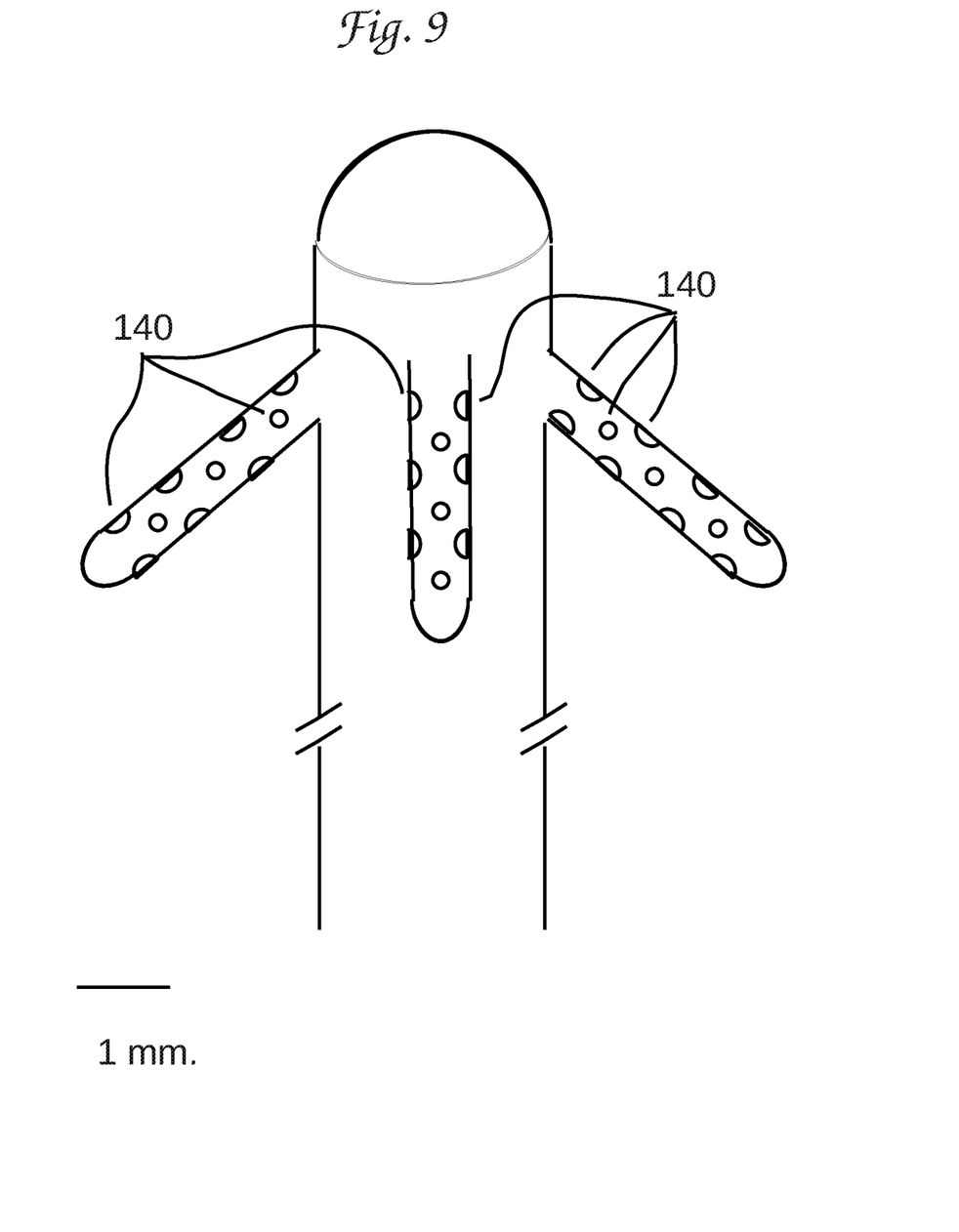
FIG. 9. A heart stimulator of the type of current art with added multiple electrodes.

In the main embodiment of my invention the microcontroller MC1, acting on instructions received by telemetry, sent by the patient, or a nurse, or a medical doctor, or any other trained medical practitioner generates the addresses of the pads that have been chosen to originate the electric pulses (see FIGS. 1 and 9) then, still inside the battery-electronics box a parallel-to-serial converter (see further description below) converts the parallel binary address lines to serial form using a specially designed hardware based on semiconductor technology. FIG. 6 shows the operation method of such a serial-to-parallel converter. Note that this invention is not the serial-to-parallel converter, which is existing art, part of the established art of digital electronics, but its combined use in a synergetic way to improve the results of deep brain stimulation (DBS). At the picafina-type electrical brain stimulator DBS, this serial information is then reconverted to parallel form which is then used to select which pads will be energized. The serial address line may be also used to carry control information from the microcontroller MC1 to the picafina ST1. FIG. 9 shows a heart stimulator of the type of current art with added multiple electrodes which add the capability of directing the stimulating electrical pulse along particular directions to create the best heart contraction sequence.

Description and Operation of Alternative Embodiments

The main embodiment described a device used for deep brain stimulation (DBS), but persons familiar with the art will recognize that many other types of electrical stimulations are also used. Cardiac electrical stimulators, known as pacemakers is the most common application. In such a case the physical structure of the stimulating structure would be different, adapted to the heart pacemaking function, yet a heart pacemaker can also be fitted with a large number of stimulating electrodes, each designated by a particular address which can be selected to be, or not to be a point of initiation of the electrical stimulation, or to be a point for measurement of electrical activity in the heart.

The main embodiment is described using a specially designed technology and protocol, but any other serial communication system is acceptable for the device of our invention, as, for example, the standard RS-232 used by older computers, or the more recent USB and FireWire, and any other standard serial communication or even one specially designed for this application. My invention is not bound to the use of a particular serial standard or technology, but rather it is based on the use of a single wire (or a small number of wires) to transmit the addresses needed to chose the electrodes within the confined space available in the supporting structure leading to the neuron, together with the standard, prior-art methods of serial-to-parallel conversion and parallel-to-serial conversion, as the persons familiar with the art of electronics and with the art of data transfer understand. The change between using a specially designed electronics to a USB technology an RS-232 technology, etc., are trivial, their differences being only speed, distance of data transmission, and the like, but using the same principle of serially transmitting the information, one bit after the other, instead of at the same time along parallel wires. Our invention is the decrease in the number of wires needed to transmit the information from the controlling device in 110 to the stimulator end of it, as a DBS picafina, superficial brain cortex stimulator, a heart pacemaker, and the likes, not the invention of serial communication, which is an old art.

Instead of having one serial-to-parallel converter associated with each plane of pads around a circle at the same distance to the ends of the picafina device, it is possible to have a serial-to-parallel converter associated with each pad. In this alternative embodiment, the number of wires in each planar cross-section, is also small, one address for each pad or electrode sent still in serial form, at the expense of having a larger number of serial-to-parallel converters: one for each pad or electrode, in this case. This alternative embodiment is possible because the actual size of the electronics is very small so the whole circuit can be made in an area of approximately 100 by 100 micrometers, which is small enough to accommodate one for each pad or electrode. These and other variations are included in the spirit of the invention, which is to have a large number of pads/electrodes, which are selected by digital addressing, while the addresses themselves are sent in serial form to accommodate the small size available for wiring from the battery pack/electronics until the actual pads/electrodes.

Another alternative embodiment is to have a small number of address lines to select for which flat, planar cross section (as in FIGS. 2 and 3) then, out of the serial-to-parallel converter only comes as many parallel lines as to select one out of the plurality of pads existing in that particular planar arrangement. For example, a picafina may contain 32 planar groupings as the planar arrangements of FIGS. 2 and 3, which are addressed with 5 digital lines (2 power 5=32), and 8 electrodes around its periphery, which are addressed with 3 digital lines (2 power 3=8). In this hypothetical arrangement the parallel address lines (the address bus) ADD 110 are 8 bits wide (5+3), the serial is as many as the particular choice is implemented, say one line only, then, at each planar group of FIGS. 2 and 3, besides the serial-to-parallel converter there exists an address decoder that decides if the particular group (on a circular cross-section on the device) is selected by the 5 lines capable of addressing the 32 planar groups. For the benefit of the biological sciences and medical readers we define here a term in common use in electronics: "to assert" in digital electronics means to make a wire on or off, as defined in each case, or a set of wires to be in any combination on and off, as needed. In this context "on" an "off" generally mean one of the two possibilities of a binary representation, as on=5V, off=0V, on=magnetic field up, off=magnetic field down, on=light, off=dark, etc. Most people use "to assert" in a more specific way, meaning to make the line H, or the bit "1". In the positive case the 3 digital lines that makes the bus A will be activated and one or more of the 8 pads in that group selected for use. In the negative case nothing is asserted in the 3 digital lines that makes the bus A for that group. This possible optional system is shown in FIG. 7. This is only another of the many possible variations that are within the scope of the invention.

Another possible variation of the invention to solve the difficult part of bringing wires down the body of the picafina, or in any other variation to bring many wires from the battery pack/electronics all the way to the large number of stimulating electrodes, is dealt with a small number of wires (one serial wire, or one wire plus ground, on a total of two wires), which are then connected to a printed circuit at each planar set of pads at fixed distance to the ends, which are connected using printed circuit (PC) technology, or chip manufacturing technology, or nanowires, or any of its equivalents, to the proximity of each pad, where a dedicated serial-to-parallel decoder decodes the serial signal is converted back to its parallel form and it is used as an address for that particular electrode pad. In this case there are a larger number of serial-to-parallel converters, but there are less parallel wires running inside the planar PC. Semiconductor electronics is inexpensive, so the price of this larger number of converters could, in certain situation be superior.

Instead of having one serial-to-parallel converter associated with each pad (with each electrode tip), or with each group of pads at a fixed distance to each end, it is possible to have a serial-to-parallel converter at the entrance of the picafina, from where multiple address wires (parallel) are distributed to each pad.

Instead of having one serial-to-parallel converter associated with each pad (with each electrode tip), it is possible to have a serial-to-parallel converter associated with each group of two pads.

Instead of having one serial-to-parallel converter associated with each pad (with each electrode tip), it is possible to have a serial-to-parallel converter associated with each group of three pads.

FIG. 9 displays a current art heart pacemaker with the added improvement of this invention, which is the possibility of multiple individually addressable electrodes, from which a better electrical current distribution can cause a better heart muscle contraction sequence, with the final objective of improving heart pumping efficiency.

The group of electrodes (pads) that is at a fixed distance to the ends of the picafina, which may be manufactured on a single monolithic die, on which the wires are printed using one of the available technologies to make PC boards (large, or wide wires), or to make chips (smaller, or narrower wires) or a combination of these, perhaps including the technology used for nanowires.

One skilled in the relevant art, however, will readily recognize that the invention can be practiced without one or more of the specific details, or with other methods, etc. In other instances, well known structures or operations are not shown in detail to avoid obscuring the features of the invention. In particular, the details of the electronics necessary for the implementation of the necessary circuits is not detailed in this patent disclosure because the actual implementation is standard use of the old art of circuit fabrication (fab) and of analog and digital electronics design.

Conclusion, Ramifications, and Scope of Invention

The parallel-to-serial electronics and logic conversion can be an RS-232-type, using any of the existing electronics chips (or the die of them), as, for example, the old Intersil HD-6402 UART chip, or the Maxim MAX3110E/MAX3111E, just to cite two examples, as this function is manufactured by many companies. Note that it is envisaged that what would be used would be the die and not the packaged chip that most consumers buy and use, due to space limitations, particularly in the picafina itself, that is in the electrode end of the device. Note that while most microcomputer implementation of the RS-232 use up to 9 lines (or wires), including multiple ground wires, not all of these are needed for serial data transfer, some computer implementations using less lines, it being possible to send data in just one wire plus ground. In our implementation of data transfer a data-wire+ground is sufficient, and a transfer of address can be made with an address-wire+ground. Such a choice minimizes development work, but our invention is not limited to it in any form. Moreover, some implementations of the electrical stimulation use the body of the wearer as ground, in which case only one wire is needed.

The serial-to-parallel and parallel-to-serial electronics and logic can be any of the many available in the market, as RS-232, RS-422, RS-423, RS-449, RS-485, USB, firewire, etc., just to mention a few examples. These are standard serial standards, which can be purchased off-the-shelf and included as part of the device, our invention being independent of the serial implementation used. It is worth mentioning that some of these standards, particularly USB, the device address is particularly easy to implement.

Another possibility is to use a reset function which, at the command of the electronics/control unit inside box 110, is capable of setting the electrodes or pads to a standard, initial state. Typically such a reset function would set all electrodes to the disconnected state, but this is only one of the available choices. The reset function could be included in the serial transmission line, in which case the serial-to-parallel converter at the stimulator side of the device (ST1) would also contain logic to separate control signals from address signals.

Another possibility is to have a combination of serial and parallel connection between 110 and ST1. In this variation, there may exist 2 wires to transfer 2 bits at a time, in a smaller number of serial steps, or 3 wires, etc.

While my above description contains many specificities, these should not be construed as limitations on the scope of the invention, but rather as an exemplification of one preferred embodiment thereof, and a few of the many possible variation of the main embodiment that still keeps its character. Many other variations are possible. For example [then continue with brief description of possible variations that aren't important enough to show as ramifications in the drawing].

Accordingly, the scope of the invention should be determined not by the embodiments illustrated, but by the appended claims, their legal equivalents and any extensions or variations that are obvious to the ones familiar with the art, as well as by the figures and drawings.

In order to avoid obscuring the features of the present invention, the main embodiment description was provided with reference to a particular parallel-to-serial and serial-to-parallel implementations. The extension to other serial transmission standard circuits will be apparent to one skilled in the relevant arts by reading the disclosure provided herein, and such implementations are contemplated to be covered by various aspects of the present invention.

One skilled in the relevant art, however, will readily recognize that the invention can be practiced without one or more of the specific details, or with other methods, etc. In other instances, well known structures or operations are not shown in detail to avoid obscuring the features of the invention.

Other possible implementations of our invention use other types of serial data transmission, as RS-232, USB, and etc. The pad address leaves the battery/electronics box in serial form using only two wires in our main embodiment (signal and return or ground), entering the picafina in this form: two wires. Inside the picafina a serial-to-parallel converter regenerates the initial binary parallel addresses (see FIGS. 5, 2, 3 and 8), which are then compared with the addresses written at each pad, to activate only the selected pads.

REFERENCES

USB hardware sources: (there are many other sources, these are only examples)
1. Source of USB host/slave controller devices:
FTDI Chip
Future Technology Devices International Limited (China)
Room 408, 317 Xianxia Road,
ChangNing District,
ShangHai, P.R. China
http://www.ftdichip.com/Tel:
Tel: +86 (21) 62351596
Fax: +86 (21) 62351595
E-Mail (Sales) cn.sales@ftdichip.com
E-mail (Support) cn.support@ftdichip.com
E-Mail (General Enquiries) cn.admin@ftdichip.com
2. Chipset for USB
Intel
http://www.intel.com/support/chipsets/sb/CS-009262.htm
3. Chipset for USB
Silicon Labs
http://www.silabs.com/products/interface/usbtouart/Pages/default.aspx
Austin, Tex. Campus
Silicon Laboratories Inc.
400 West Cesar Chavez Austin, Tex. 78701
USA
phone: 512.416.8500
toll-free: 877.444.3032
sales fax: 512.416.9669

USB references/general information (selected web page sources):
http://www.usbmadesimple.co.uk/index.html
http://www.usb.org/home
http://en.wikipedia.org/wiki/Universal_Serial_Bus
http://www.beyondlogic.org/usbnutshell/usb2.htm Cables'Electrical USB requires a shielded cable containing 4 wires.

Two of these, D+ and D−, form a twisted pair responsible for carrying a differential data signal, as well as some single-ended signal states. (For low speed the data lines may not be twisted.)

The signals on these two wires are referenced to the (third) GND wire.

The fourth wire is called VBUS, and carries a nominal 5V supply, which may be used by a device for power.

RS-232 serial connectors and standards, hardware and software:
1. http://en.wikipedia.org/wiki/RS-232
2. http://www.maxim-ic.com/quick_view2.cfm?pdf_num=2052

The MAX3110E/MAX3111E combine a full-featured universal asynchronous receiver/transmitter (UART) with ±15 kV ESD-protected RS-232 transceivers 3. http://www.national.com/mpf/PC/PC16550D.html#Overview

PC16550D

Universal Asynchronous Receiver/Transmitter with FIFO's

MODEM control functions (CTS, RTS, DSR, DTR, RI, and DCD).

Fully programmable serial-interface characteristics:
5-, 6-, 7-, or 8-bit characters
Even, odd, or no-parity bit generation and detection
1-, 1½-, or 2-stop bit generation
Baud generation (DC to 1.5M baud).
False start bit detection.

Medtronic (n/d) Medtronic
StJude (n/d) St. Jude Medical (add webpage)
Paul Horowitz and Hill "The Art of Electronics" ($1^{st}$ and $2^{nd}$ editions), Cambridge University Press, Cambridge, Mass.
Jan Axelson "USB Complete—Everything You Need to Develop Custom USB Peripherals" Lakeview Research (1999)
Jan Axelson "Parallel Port Complete—Programming, Interfacing, & Using the PC's Parallel Printer Port" Lakeview Research (1997)
Harvey_2007 Harvey R L, Nudo R J. "Cortical brain stimulation: a potential therapeutic agent for upper limb motor recovery following stroke." *Top Stroke Rehabil.* 2007 November-December; 14(6):54-67
Kandel_2000, Eric R. Kandel et al., "Principles of Neuroscience" (2000), several editions. This book is a bible in the field of neurosciences.

The invention claimed is:

1. A non-transitory computer readable medium for use on a computer system for measuring and/or stimulating electrodes in a multichannel electrode array, each of the electrodes having a unique binary address, the multichannel electrode array being electrically connected to multiple carrying wires configured to transfer a multiplicity of levels of electric currents and/or voltages, each of the wires having a unique binary address, the computer system also having at least one wire configured to transfer serial format binary numbers, the non-transitory computer readable medium comprising a non-transitory computer readable medium having computer readable program code thereon, the computer readable program code including:
program code for determining a binary address of at least one of the electrodes in the multichannel electrode array to becoming active for electrical activity measurement, and/or;
program code for determining a binary address of at least one of the electrodes in the multichannel electrode array to becoming active for electrical stimulation;
program code for determining a binary address of at least one of the carrying wires configured to transferring the electric energy amplitude;
wherein the selection of the electrodes for electric activity measurement and/or for electrical stimulation is made by the non-transitory computer readable medium according to the spatial positioning of the electrodes and the selection of the carrying wires is made according to the requirement to transfer different electric energy level amplitudes;
wherein the non-transitory computer readable medium further includes program code for calculating the electric field created by the activated electrodes.

2. The non-transitory computer readable medium according to claim 1, wherein the program code further includes program code for selecting the electrodes for measurement, wherein the measurements are used for determining the optimal choice of the electrical stimulation.

3. The non-transitory computer readable medium according to claim 1, wherein the program code further includes program code for selecting the electrodes for stimulation according to the effects of the electric stimulation as observed by an external medical personnel and/or by an external researcher personnel.

4. The non-transitory computer readable medium according to claim 1, wherein more than one of the electrodes is simultaneously selected for stimulation and the stimulation is at different levels of electric current and/or voltage.

* * * * *